US010198668B2

(12) United States Patent
Ryu et al.

(10) Patent No.: US 10,198,668 B2
(45) Date of Patent: Feb. 5, 2019

(54) APPARATUS AND METHOD FOR SUPPORTING COMPUTER AIDED DIAGNOSIS (CAD) BASED ON PROBE SPEED

(71) Applicant: SAMSUNG ELECTRONICS CO., LTD., Suwon-si (KR)

(72) Inventors: Seung Woo Ryu, Seoul (KR); Yeong Kyeong Seong, Yongin-si (KR); Kyoung Gu Woo, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 159 days.

(21) Appl. No.: 14/795,027

(22) Filed: Jul. 9, 2015

(65) Prior Publication Data

US 2016/0019441 A1    Jan. 21, 2016

(30) Foreign Application Priority Data

Jul. 16, 2014  (KR) .................. 10-2014-0090017

(51) Int. Cl.
*G06K 9/62* (2006.01)
*G06T 7/00* (2017.01)
(Continued)

(52) U.S. Cl.
CPC ............ *G06K 9/6267* (2013.01); *A61B 8/085* (2013.01); *A61B 8/469* (2013.01); *A61B 8/5207* (2013.01); *A61B 8/5223* (2013.01); *G06K 9/4642* (2013.01); *G06K 9/6215* (2013.01); *G06T 7/0012* (2013.01); *A61B 8/0825* (2013.01); *A61B 8/4245* (2013.01); *A61B 8/5246* (2013.01); *G06K 2009/4666* (2013.01);
(Continued)

(58) Field of Classification Search
None
See application file for complete search history.

(56) References Cited

U.S. PATENT DOCUMENTS 8,600,133 B2    12/2013  Buelow et al.
2003/0048312 A1  3/2003  Zimmerman et al.
(Continued)

FOREIGN PATENT DOCUMENTS

JP    2000-194736 A    7/2000
JP    2006-301654 A    11/2006
(Continued)

OTHER PUBLICATIONS

Extended European Search Report dated Nov. 26, 2015 in counterpart European Application No. 15174275.6 (8 pages, in English).
(Continued)

*Primary Examiner* — Matthew Bella
*Assistant Examiner* — Brian Shin
(74) *Attorney, Agent, or Firm* — Jefferson IP Law, LLP

(57) ABSTRACT

There is provided an apparatus for supporting Computer Aided Diagnosis (CAD) based on a speed of a probe. The apparatus includes a region of interest (ROI) detector configured to detect an ROI from a current image acquired from a probe; and an ROI classifier configured to determine whether to classify the ROI using a determined state of a speed, and classify the ROI according to a result of the determination.

14 Claims, 13 Drawing Sheets

(51) Int. Cl.
*A61B 8/08* (2006.01)
*A61B 8/00* (2006.01)
*G16H 50/20* (2018.01)
*G06K 9/46* (2006.01)

(52) U.S. Cl.
CPC ............... *G06T 2207/10132* (2013.01); *G06T 2207/30096* (2013.01); *G16H 50/20* (2018.01)

(56) References Cited

U.S. PATENT DOCUMENTS

| | | |
|---|---|---|
| 2006/0092133 A1 | 5/2006 | Touma et al. |
| 2007/0010743 A1* | 1/2007 | Arai ................. A61B 8/13 600/443 |
| 2007/0126696 A1 | 6/2007 | Boillot |
| 2009/0327974 A1 | 12/2009 | Abanami et al. |
| 2012/0116219 A1 | 5/2012 | Miller et al. |
| 2012/0232390 A1 | 9/2012 | Park |
| 2012/0249475 A1 | 10/2012 | Murphy et al. |
| 2013/0245428 A1 | 9/2013 | Banjanin et al. |
| 2015/0148657 A1* | 5/2015 | Shashar ............... A61B 8/0866 600/408 |

FOREIGN PATENT DOCUMENTS

| | | |
|---|---|---|
| KR | 10-2012-0020045 A | 3/2012 |
| WO | WO 2013/183051 A1 | 12/2013 |

OTHER PUBLICATIONS

Jong-Oh Kim et al.; "Gesture User Interface for Controlling Objects in the 3D Virtual Space"; Department of Digital Informatics and Convergence, Chungbuk National University; khyoo@chungbuk.ac.kr; 2012; pp. 103 and 104.

* cited by examiner

APPARATUS AND METHOD FOR SUPPORTING COMPUTER AIDED DIAGNOSIS (CAD) BASED ON PROBE SPEED

CROSS-REFERENCE TO RELATED APPLICATION(S)

This application claims the benefit under 35 USC 119(a) of Korean Patent Application No. 10-2014-0090017 filed on Jul. 16, 2014 in the Korean Intellectual Property Office, the entire disclosure of which is incorporated herein by reference for all purposes.

BACKGROUND

1. Field

The following description relates to an apparatus and method for supporting Computer Aided Diagnosis (CAD), based on a probe speed, for detection and determination of a lesion.

2. Description of Related Art

In the medical field, it is common to examine a patient by analyzing ultrasonic images. Such ultrasonic images allow visualization of internal body structures, such as organs, blood vessels, and muscles. Ultrasound refers to sound waves that have a frequency too high for human beings to hear. Generally, doctors acquire ultrasonic images in real time by putting a probe in contact with a patient's body, known as a transducer. The transducer sends pulses of ultrasound into tissue within the patient's body, and the ultrasound pulses reflect from the interior of the patient's body. Because different types of tissue reflect ultrasound in different ways, by tracking and analyzing the echoes that occur when the ultrasound is reflected, it is possible to produce an image that corresponds to the interior of the patient's body. By reviewing such images, it is possible for a radiologist or another medical professional to detect and determine a lesion or a suspicious area by monitoring the ultrasonic images output on a screen. When an area suspected as a lesion is found, a doctor slowly moves or stops moving the probe to observe the area. By doing so, the probe provides an image of the area of interest. Ultrasonography has advantages over other forms of imaging, in that it can be done in real-time, is relatively inexpensive, and does not involve potentially hazardous radiation. However, ultrasound also potentially has problems imaging structures such as bone, and successful ultrasound imaging requires a skilled operator who is able to position the transducer properly.

A Computer Aided Diagnosis (CAD) system analyzes an ultrasonic image acquired by a probe, detects a lesion by processing the ultrasonic image, and then either tracks the lesion or implements detection and classification on the lesion with respect to each ultrasonic image. By considering a lesion in this manner, such a CAD system is able to make a determination with respect to the malignancy/benignancy of the lesion. For example, if there is a cancerous growth on a user's organ, a CAD system may be able to determine from considering characteristics of the ultrasound image whether the growth is dangerous or not. Based on such a determination, it may be possible to produce treatment recommendations, such as whether it is appropriate to perform surgery to remove a certain growth, or if chemotherapy or radiation therapy is necessary. However, a CAD system's computing performance plays as a key role in analyzing images. At present, CAD systems require time to process and analyze ultrasound images to derive diagnoses based on the images. The computing demands involved in such systems limit rapid analysis of ultrasonic images acquired by a probe. Hence, diagnoses are not completely convenient because the diagnoses are not available at the time of scanning, but instead must be produced for subsequent use.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an apparatus to support Computer Aided Diagnosis (CAD) includes an image acquirer configured to acquire an image from a probe, a speed determiner configured to detect a speed of the probe and to determine a state of the detected speed, a region of interest (ROI) detector configured to detect an ROI from a current image acquired from the probe, and an ROI classifier configured to determine whether to classify the ROI using the determined state of the speed, and to classify the ROI according to a result of the determination.

The speed determiner may be further configured to detect the speed using a change between images acquired from the probe.

The change between images may include a difference in sums of image intensity for each pixel between the current image and a previous image, a difference in histograms between the current image and the previous image, a similarity in histograms between the current image and the previous image, or a degree of change in primary information between the currently acquired image and the previously acquired image.

The speed determiner may be further configured to compare the detected speed to a preset threshold and to determine the state of the detected speed as being one of a halted state, a low speed state, or a high speed state.

In a case where the determined state of the speed is a high speed state, the ROI detector may extract feature information from the current image and detects the ROI using the feature information.

In a case where the determined state of the speed is a halted state or a low speed state, the ROI detector may detect the ROI by determining an area to be searched in the current image using information on an area searched in the previous image or using information on an ROI extracted from the previous image and extracting feature information from the area to be searched in the current image.

The ROI classifier may be further configured to, in a case where the state of the detected speed is a halted state or a low speed state, determine to classify the ROI, extract feature information from the current image, and to classify the ROI using the extracted feature information.

The apparatus may further include a display configured to output the current image on a screen, and, in response to detecting an ROI from the current image, to output a distinguished marker indicative of the ROI at a corresponding location in the current image on the screen using location information of the ROI.

The display may be further configured to, in a case where the determined state of the speed is a halted state or a low speed state, output the distinguished marker at the corresponding location in the current image on the screen using location information of an ROI detected from an image previous to the current image.

The display may be further configured to, in response to classification being performed on the ROI, output a classification result on a specific location on the screen or output the classification result so as to overlap the current image on the screen.

The display may be further configured to output an information item indicative of the detected speed, the determined state of the speed, or a current diagnostic process.

In another general aspect, a method to support Computer Aided Diagnosis (CAD) includes acquiring an image from a probe, detecting a speed of the probe, determining a state of the speed, detecting a region of interest (ROI) from a current image, determining whether to classify the ROI using the state of the speed, and classifying the ROI according to a result of the determination.

The detecting of speed may include detecting the speed using a change between images acquired from the probe.

The change between images may include a difference in sums of image intensity for each pixel between the current image and a previous image, a difference in histograms between the current image and the previous image, a similarity in histograms between the current image and the previous image, or a degree of change in primary information between the current image and the previous image.

The determining of a state of the speed may include comparing the speed to a preset threshold and determining the state of the speed as being one of a halted state, a low speed state, or a high speed state.

The detecting of an ROI may include, in a case where the state of the speed is determined to be a high speed state, extracting feature information from the current image, and detecting an ROI using the extracted feature information.

The detecting of an ROI may include, in a case where the state of the speed is determined as a halted state or a low speed state, determining an area to be searched in the current image using information on an area searched in the previous image or using information on an ROI detected from the previous image, extracting feature information from the determined area to be searched in the current image, and detecting the ROI using the extracted feature information.

The determining of whether to classify the ROI may include determining to classify the ROI in response to the state of the speed being determined as a halted state or a low speed state, wherein the classifying of the ROI includes in response to a determination to classify the ROI, extracting feature information, and classifying the ROI using the extracted feature information.

The method may further include outputting the current image on a screen, and in response to detecting an ROI from the current image, outputting a distinguished marker indicative of the ROI at a corresponding location in the current image on the screen using location information of the ROI.

The outputting of a distinguished marker may include, in a case where the state of the speed is a halted state or a low speed, outputting the distinguished marker indicative of the ROI at the corresponding location in the current image on the screen using location information of an ROI detected from the previous image.

The classifying of the ROI may include, in response to classification being implemented on the ROI, outputting a classification result of the ROI at a specific location on a screen or outputting the classification result of the ROI so as to overlap the current image on the screen.

The method may further include outputting information indicative of a diagnostic process that is currently performed on the current image.

In another general aspect, an apparatus to support Computer Aided Diagnosis (CAD) includes a speed determiner configured to detect speed of a probe and to determine a state of the speed, a process selector configured to, using the determined state of the speed, select a process of detecting a region of interest (ROI), a process of classifying an ROI, or a process of detecting and classifying an ROI, and an ROI processor configured to perform the selected process on a current image acquired by the probe.

The speed determiner may compare the speed with a preset threshold and determine the state of the speed as being one of a halted state, a low speed state, or a high speed state.

The process selector may be further configured to select the process of detecting an ROI as the process to be performed on the current image in a case where the state of the speed is determined to be a high speed state, and in accordance with a preset policy, select the process of classifying an ROI or the process of detecting and classifying an ROI in a case where the state of the speed is determined to be a halted state or a low speed state.

The ROI processor may be further configured to, in a case where the state of the speed is determined to be a halted state or a low speed state and the process of detecting and classifying an ROI is selected, to detect an ROI from the current image using information on an area searched in the previous image or information on an ROI detected from the previous image.

The apparatus may further include a display configured to output, on a screen, a current image acquired from the probe, output on the screen at least one of the speed of the probe and the determined state of the speed, and to output, on the screen, information on a process that is currently performed on the current image using information on the selected process.

In another general aspect, a method to support Computer Aided Diagnosis (CAD) includes detecting a speed of a probe, determining a state of the speed, using the determined state of the speed, selecting a process of detecting a region of interest (ROI), a process of classifying an ROI, or a process of detecting or classifying an ROI, and performing the selected process on a current image acquired by the probe.

The determining of a state of the speed may include comparing the speed with a preset threshold and determining the speed as being one of a halted state, a low speed state, or a high speed state.

The selecting of one of a halted state, a low speed state, or a high speed state may include selecting the process of detecting an ROI as a process to be performed on the current image in a case where the state of the speed is determined to be a high speed state, and in accordance with a preset policy, selecting the process of classifying an ROI or the process of detecting and classifying an ROI in a case where the state of the speed is determined to be a halted state or a low speed state.

The performing of the selected process may include, in a case where the state of the speed is determined to be a halted state or a low speed state and the process of detecting and classifying is selected, detecting an ROI from the current image using information on an area searched in a previous image or information on an ROI detected from the previous image.

The method may further include outputting on a screen the current image acquired by the probe, outputting on the screen at least one of the speed of the probe and the state of the speed, and outputting, on the screen, information on a process that is currently performed on the current image using information on the selected process.

In another general aspect, an apparatus to support Computer Aided Diagnosis (CAD) includes a region of interest (ROI) detector configured to detect an ROI from a current image acquired from a probe, and an ROI classifier configured to determine whether to classify the ROI using a determined state of a speed of the probe, and to classify the ROI according to a result of the determination.

The apparatus may further include an image acquirer configured to acquire an image a probe.

The apparatus may further include a speed determiner configured to detect a speed of the probe and to determine a state of the detected speed.

The speed determiner may be further configured to detect the speed using a change between images acquired from the probe.

The speed determiner may further configured to compare the detected speed to a preset threshold and to determine the state of the detected speed as being one of a halted state, a low speed state, or a high speed state.

In a case where the determined state of the speed is a high speed state, the ROI detector may extract feature information from the current image and detects the ROI using the feature information.

The apparatus may include a display configured to output the current image on a screen, and, in response to detecting an ROI from the current image, to output a distinguished marker indicative of the ROI at a corresponding location in the current image on the screen using location information of the ROI.

Other features and aspects will be apparent from the following detailed description, the drawings, and the claims.

BRIEF DESCRIPTION OF THE DRAWINGS

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Hereinafter, an apparatus and method for supporting Computer Aided Diagnosis (CAD) based on a probe speed are described further with reference to the figures. However, the application merely presents certain examples, and it is intended to be recognized that other examples are possible, as well.

Figure 1:
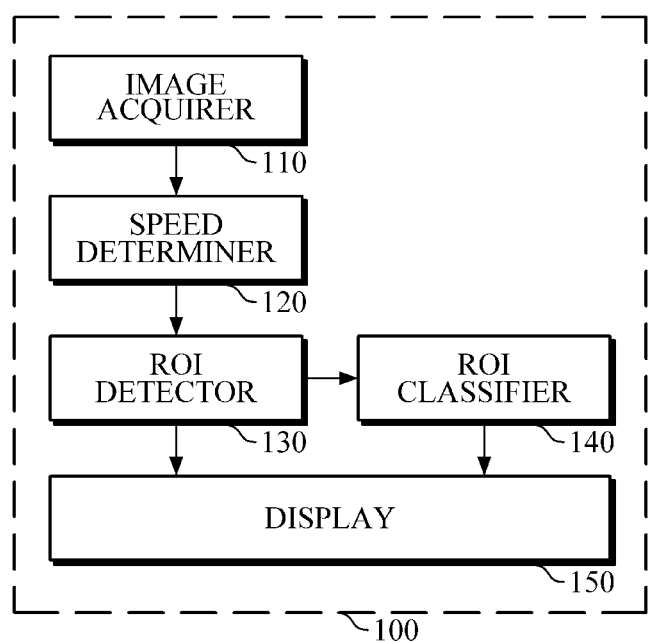
FIG. 1 is a block diagram illustrating an apparatus for supporting Computer Aided Diagnosis (CAD) according to an example.
Figure 2:
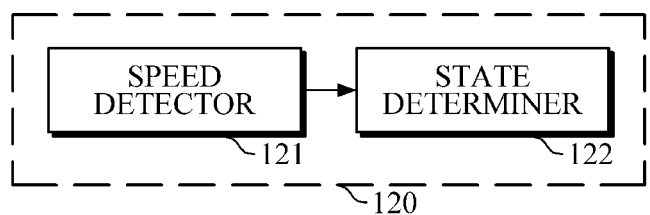
FIG. 2 is a diagram illustrating a speed determiner as shown in FIG. 1.

FIG. 1 is a block diagram illustrating an apparatus for supporting CAD according to an example. FIG. 2 is a diagram illustrating a speed determiner as shown in FIG. 1.

An apparatus 100 for supporting CAD according to the example of FIG. 1 is a device that analyzes an image, for example, an ultrasonic image, received in real-time from a probe, and detects a Region of Interest (ROI) from the image, providing a diagnostic result of the ROI. As discussed above, such images are produced by using a probe, known as a transducer, that projects ultrasound into a patient and receives the echoes of such projected ultrasound. By using algorithms and techniques to process the raw reflected data, the apparatus 100 generates images. The images are subsequently processed in a way that establishes the structure of the interior of the patient onto which the ultrasound is projected.

Referring to the example of FIG. 1, the apparatus 100 includes an image receiver 110, a speed determiner 120, an ROI detector 130, an ROI classifier 140, and a display 150. However, these components of the apparatus 100 are merely examples, and it is to be noted that in other examples other appropriate components are optionally used instead of or in addition to these components.

When the apparatus 100 is being used, a user performs diagnosis using a probe in contact with a patient's body. In this scenario, the user is an operator of the ultrasound apparatus 100, generally a medical professional who has been trained to properly position the transducer so as to gather useful information based on the results of positioning the probe close to or upon the patient's body so as to direct the ultrasound emitted from the probe so that the apparatus is able to gather useful information. For example, once the user has positioned the probe, the image receiver 110 receives an ultrasonic image of the patient's body from the probe. In an example, the image receiver 110 receives an image from the probe in real time. In such an example, the real time operation of the probe is based on rapidly gathering information corresponding to ultrasound echoes, and then analyzing that information quickly enough that rather than having to wait a long time to accumulate image data, such as in Magnetic Resonance Imaging (MRI). In addition, in an example, the image receiver receives images from the probe in a sequence in units of frames. By accumulating images quickly in real time in this manner, it is not only possible to rapidly produce an image of the interior of a patient's body, but it is also possible to track changes within a patient's body over time by producing sequential images that represent images corresponding to a succession of instants in time.

When the user, as discussed above, performs a diagnostic procedure with a probe in contact with the patient's body, the speed determiner 120 detects a movement speed of the probe and determines a speed state. By tracking a movement speed of the probe in this manner, the speed determiner 120 is able to characterize the movement of the probe in a manner that gives additional context and meaning to how the probe is moved, such that by considering information about the probe's motion when analyzing the sequence of ultrasound images, the motion information provides context for the ultrasound images and gives additional images about which parts of the patient's body they depict. This contextual information, which is also derived in real time, assists in the process of trying to identify and diagnose lesions. Referring to the example of FIG. 2, the speed determiner 120 includes a speed detector 121 and a state determiner 122. However, this is only one example of a speed determiner 120 and a speed determiner 120, in other examples, includes other components in addition to or instead of these components.

When the user moves the probe in contact with the patient's body to diagnose the patient, the speed detector 121 detects a moving speed of the probe. Here, moving speed is simply a measure of the distance that the speed detector is moved divided by the time it takes to move the speed detector that distance. Here, the speed detector 121 is configured to measure speed, and does not necessarily consider the direction in which the probe is moved. For example, in order to determine the speed of motion of the probe, in one example, the speed detector 121 detects the speed of the probe based on a change in images received by the probe, that is, a change between a previous image and the current image. For example, if two images share common features, considering the change in how the features are portrayed in multiple images allows the speed detector 121 to deduce a motion speed for the probe. Accordingly, the change in images is determined in units of frames. That is, by determining a change between a previously received frame and the currently received frame, the speed detector 121 detects a moving speed of a probe.

For example, the speed detector 121 detects a speed of the probe by using differences in sums of image intensity for each pixel between the current image and a previous image as indicating a change between images. That is, if an image is acquired by the probe, the speed detector 121 performs pre-processing on the acquired image to measure image intensity for each pixel. The speed detector 121 then calculates a sum of image intensity for each pixel of the acquired image. In such an example, the speed detector 121 calculates displacement for a predetermined period of time using the sum of image intensity, and detects a speed of the probe based on the calculated displacement.

In another example, the speed detector 121 detects a speed of the probe by comparing histograms for a previous image and the current image. For example, based on a difference or similarity in histograms between a previous image and the current image, the speed detector 121 detects a speed of the probe. To this end, the speed detector 121 generates a histogram of each image using frequency values of each pixel value extracted from the entire image or a specific part of the image. Then, if a difference or similarity in frequencies of the generated histograms is greater than a predetermined level, the speed detector 121 detects a probe speed based on the generated difference or similarity.

In yet another example, the speed detector 121 detects a probe speed based on a degree of change in primary information between a previous image and the current image. For example, the primary information of an image includes information on a salient region.

Meanwhile, as an alternative or an additional means of determining the probe speed, the probe optionally includes a three-axis accelerometer or another sensor that helps detect the motion of the probe. For example, a laser motion sensor is an alternative way of tracking the probe's motion that is potentially used in another example. As an additional or alternative was of tracking the movement of the probe, the speed detector 121 detects a moving speed of a probe using the three-axis accelerometer or alternative sensor.

In response to detection of the moving speed of the probe, the state determiner 122 determines a speed state. For example, as shown in Table 1, the state determiner 122 compares the detected moving speed with a predetermined threshold for speed and determines the detected speed as halt, low speed, or high speed. Herein, the threshold is predetermined by various standards considering performance of a device or the like.

TABLE 1

| Threshold (unit: cm/sec) | Speed State |
|---|---|
| less than 0.5 | halt |
| more than 0.5, less than 3 | low |
| more than 3 | high |

Again, referring to the example of FIG. 1, the ROI detector 130 detects an ROI from an image acquired by the probe by performing a process of detecting an ROI from an image. In addition, when the ROI is detected, the ROI detector 130 tracks the ROI. Herein, in an example, the ROI includes a lesion or an area suspected to be a lesion.

In this example, the ROI detector 130 extracts feature information from the image currently received by the probe, and detects an ROI based on the extracted feature information. At this point, the ROI detector 130 detects the ROI by searching for an area that is suspected to be a lesion or by performing segmentation on a lesion.

Herein, feature information of an ROI is a value of features, such as features of a lesion, which are extracted by performing image data processing on an image, and the features of a lesion indicate features that enable determination as to whether the ROI in the image is a lesion or not. In various examples, the feature information includes a morphological feature, such as Histogram of Orientation (HoG) information, scale-invariant feature transform (SIFT) information, Speeded Up Robust Features (SURF) information, Blob, or similar information. Examples of a morphological feature also include information such as shape, margin, and boundary information, and a computer-recognizable value, such as texture.

According to an exemplary embodiment, the ROI detector 130 extracts feature information from the entire area of an image currently received by a probe, and detects an area suspected to be a lesion based on the extracted feature information. That is, in a case where a user receives an image in real time by examining a patient's body using a probe, the ROI detector 130 automatically extracts feature information from the image, which is received in real time, and detects a lesion or an area suspected to be a lesion based on the feature information.

Figure 3A:
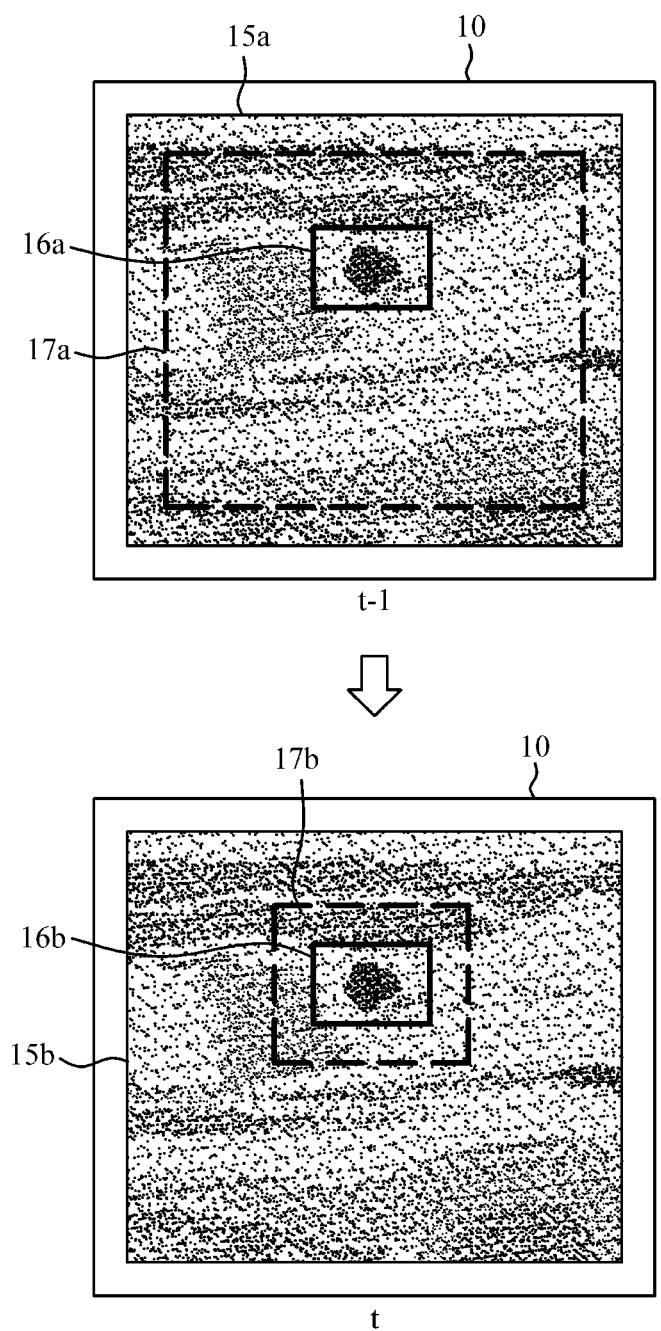
FIG. 3A is a diagram illustrating an example of how to detect a region of interest (ROI).

FIG. 3A is an example of a process of detecting an ROI. Referring to the example of FIG. 3A, the ROI detector 130 detects an ROI based on a speed state determined by the speed determiner 120, as discussed further above.

For example, in a case where a speed state is a high speed state, the ROI detector 130 detects an ROI by extracting feature information from the current image 15b, for example, the current frame t. In a case where a speed state is a halted state or a low speed state, the ROI detector 130 detects an ROI 16b from the current image 15b based on location information of a previous image 15a, as shown in the upper part of FIG. 3A. At this point in time, the ROI detector 130 determines an area 17b to be searched in the current image 15b, based on the location information of the previous image 15a. However, the ROI detector 130 also extracts feature information of the area 17b to be searched in the current image 15b. Thus, at this point, the location information of the previous image 15a includes location information of an area 17a that was searched in the previous image 15a, location information of an ROI 16a that was detected from the previous image 15a, and the like. By processing the images in this manner, the ROI detector 130 is able to improve performance by minimizing unnecessary and redundant processing.

According to this example, in a case where a speed state is a halted state or a low speed state, the previous image 15a and the current image 15b are highly likely to be less different from each other, because the probe has not been moved or only moved minimally. As a result, the ROI detector 130 extracts feature information only on an area 17b in the current image 15b, where a change is expected, and detect an ROI 16b from the current image 15b based on information of the ROI 16a detected from the previous image. By doing so, the size of the area 17b that is to be processed for feature extraction is significantly reduced compared to the area 17a. Thus, time for detecting a lesion is potentially significantly reduced because there is less information to be processed by the ROI detector 130.

Again, referring to the example of FIG. 1, the ROI classifier 140 determines whether to classify an ROI based on the speed state determined by the speed determiner 120. For example, the ROI classifier 140 determines to classify an ROI in a case where a speed state is a halted state or a low speed, so that the ROI classifier 140 classifies an ROI detected by the ROI detector 130. In addition, in this example, the ROI classifier 140 determines not to classify an ROI in a case where a speed state is determined as being high speed, so that the ROI classifier 140 does not classify an ROI with respect to the current image that is acquired at a high speed. As discussed above, when an image is acquired at high speed, there are likely to be more differences in the region under consideration and hence reusing previous results is not appropriate.

For example, in a case where a speed state is a halted state or a low speed state, the ROI classifier 140 classifies an ROI to determine whether a lesion is benign or malignant. In addition, in an example for a case of breast imaging, the ROI classifier 130 computes information on Breast Imaging-Reporting And Data System (BI-RADS) lexicon classification of a lesion, additional feature information, morphological information, and other related information. However, these are only examples of diagnostic information, and the ROI classifier generates other information in other examples. At this point, the ROI classifier 140 further extracts feature information necessary to classify an ROI in the current image, for example, the current frame (t).

As such, according to an exemplary embodiment, a process of detecting and tracking an ROI in an image is performed in a case where speed of a probe is fast, while a process of detecting, tracking, and classifying an ROI is performed in a case where the speed is slow.

According to another example, a process of detecting and tracking an ROI in an image is performed in a case where speed of a probe is fast. However, a process of classifying an ROI is performed by utilizing location information of an ROI detected from a previous image and by extracting feature information of the ROI detected from the current image in a case where the speed is slow or if there is no motion.

Meanwhile, as described above, in the process of detecting an ROI when the speed is slow, the ROI detector 130 detects an ROI from the current image by utilizing feature information and location information of an ROI detected from a previous image. Further, the ROI classifier 140 classifies the ROI by extracting additional feature information from the current image, which is necessary to classify the ROI. Using this approach achieves avoidance of performance degradation of diagnostic performance as much as possible while also reducing processing demands.

Again, referring to the example of FIG. 1, the display 150 performs an interface function that enables outputting relevant information on a screen for a user and receiving information input by the user. When the user captures a patient's body by moving a probe, as discussed above, the display 150 output an image received from the probe. As discussed, such an image is a graphical representation of image information gathered based on echoes of ultrasound projected into the patient's body.

Figure 3B:
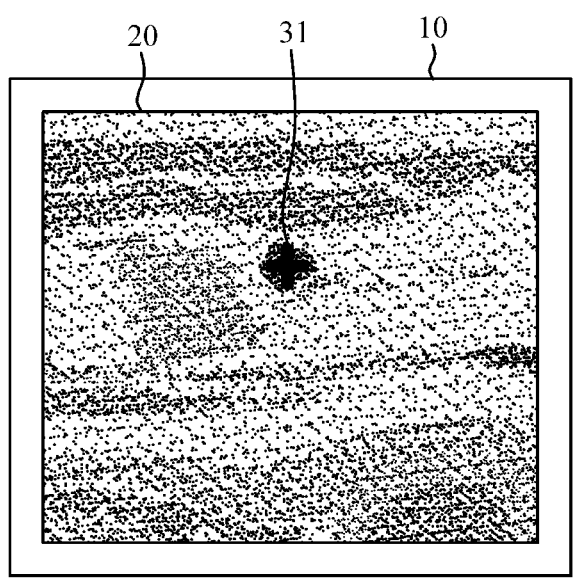
FIGS. 3B and 3C are diagrams illustrating examples of how to display an ROI on a screen.
Figure 3C:
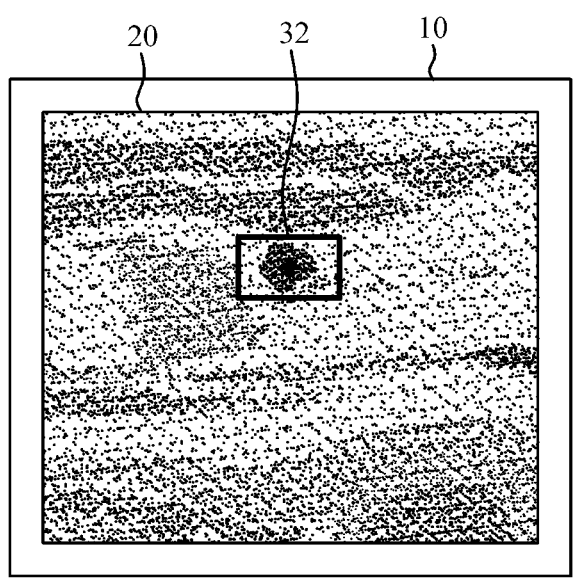
Figure 4A:
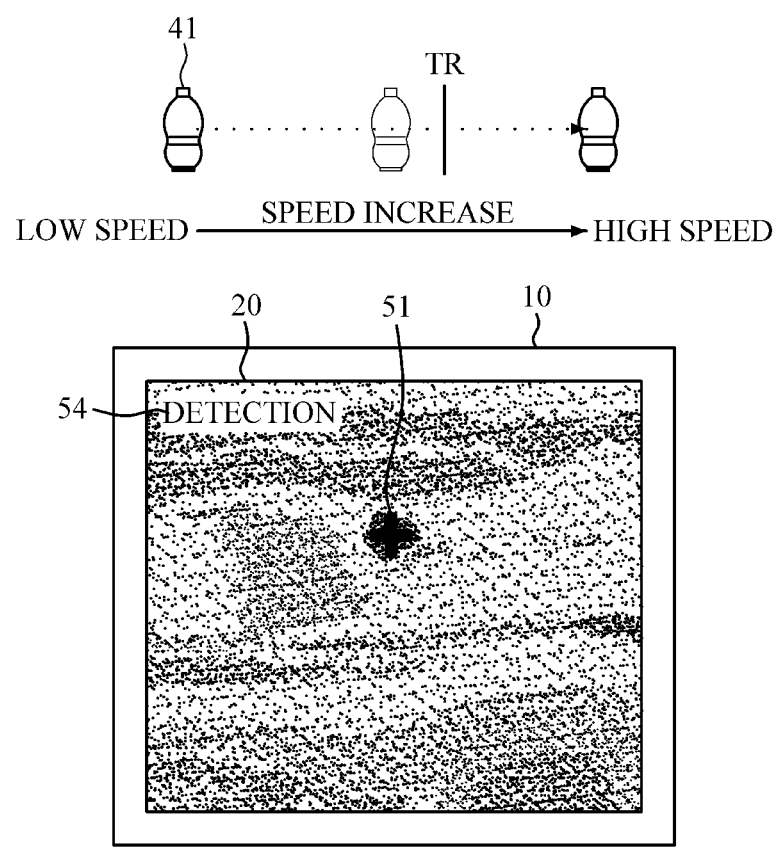
FIGS. 4A, 4B and 4C are diagrams illustrating examples of detecting an ROI and outputting a result of determination according to a speed of a probe.
Figure 4B:
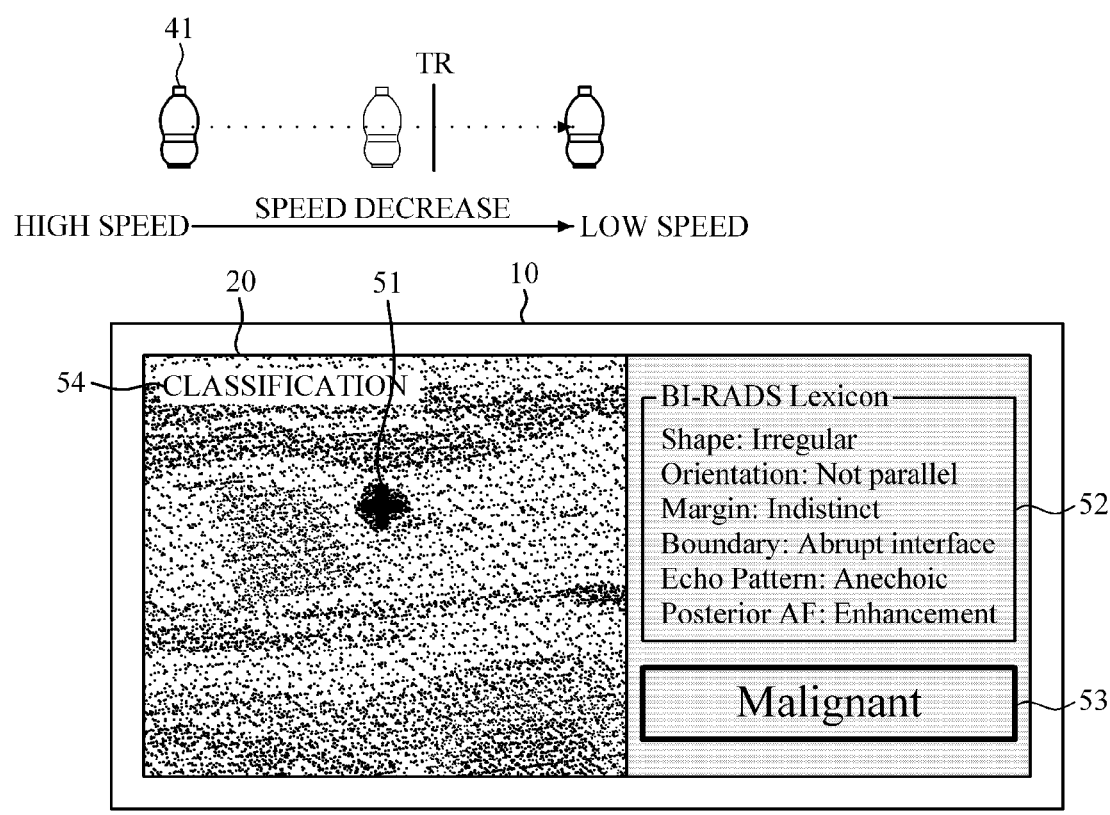
Figure 4C:
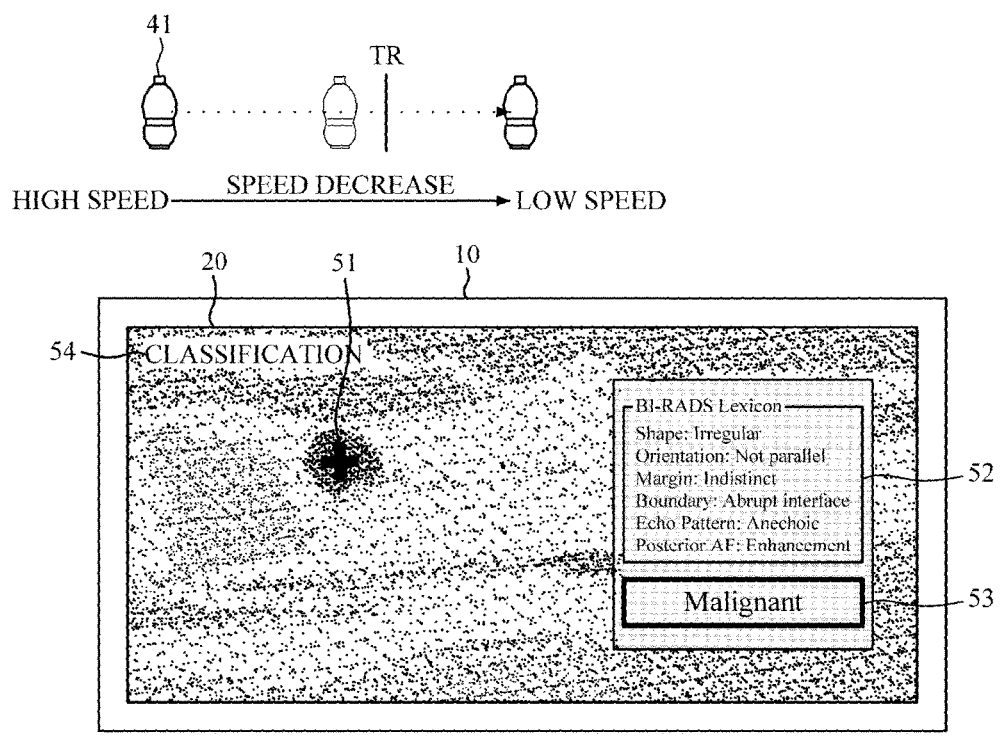

FIGS. 3B and 3C are examples of a process of displaying an ROI in an image acquired by a probe. FIGS. 4A, 4B, and 4C are examples of a process of detecting an ROI and classifying the ROI based on a probe speed.

Referring to the examples of FIGS. 1, 3B, and 3C, the display 150 outputs an ROI detected by the ROI detector 130 in various predetermined ways, whereby a user is allowed to visually recognize the detected ROI. For example, as illustrated in the examples of FIGS. 3A and 3B, the display 150 displays a location of an ROI by outputting specific distinguished markers 31 and 32 at locations corresponding to ROIs detected from an image 10 that are output on a screen 10. FIG. 3B is an example in which the distinguished marker 31 in a form of a cross is output at a location of an ROI, and FIG. 3C is an example in which the distinguished marker 32 in a form of a square is output at a location of an ROI. However, examples are not limited thereto, and a distinguished marker may be a circle, a square, and any other form of various colors and sizes in various other examples.

Referring to the examples of FIGS. 4A, 4B, and 4C, the display 150 outputs either or both of a detected ROI and a classification result thereof according to a probe speed, that is, a speed state determined by the speed determiner 120. At this point in time, according to a speed state, the display 150 outputs, at a specific location on the screen, a current process of detecting or classifying an ROI.

For example, as illustrated in the upper part of FIG. 4A, in a case where speed of a probe 41 gradually increases from a halted state or a low speed state to a high speed state greater than a threshold TR, the ROI detector 130 detects an ROI but the ROI classifier 140 does not classify the ROI. At this point, as illustrated in the lower part of FIG. 4A, the display 150 outputs a distinguished marker 51, where the distinguished marker 51 is indicative of an ROI detected by the ROI detector 120, in an image 20 on the screen 10. In addition, in an example, the display 150 outputs, in the upper part of the screen, information 54 indicating that a process of detecting an ROI is in progress.

In another example, as illustrated in the upper parts of FIGS. 4B and 4C, in a case where speed of the probe 41 gradually decreases to a lower speed state smaller than the threshold TR or a halted state, the ROI detector 130 detects an ROI and the ROI classifier 140 classifies the ROI. At this point in time, as illustrated in the lower parts of FIGS. 4B and 4C, the display 150 outputs the distinguished marker 51, which is indicative of a location of the detected ROI in the image 20 output on the screen 10. In addition, in this example, the display 150 outputs, on the upper part of the screen, information 54 that indicates that a process of classifying an ROI is in progress. Further, in such an example, the display 150 outputs the feature information 52 and a classification result 53 around the ROI, by outputting the feature information 52 and the classification result 53 at a specific location on the screen, for example, an area that is distinguished from an area where the image 20 is output on the screen, or by overlapping the same information with the image 20, as shown in FIG. 4C.

Although not illustrated in the drawings, the display 150 optionally displays speed on a screen in a case where the speed is determined by the speed determiner 120, and, if a state of the speed is determined, outputs the speed state on the screen.

Figure 5:
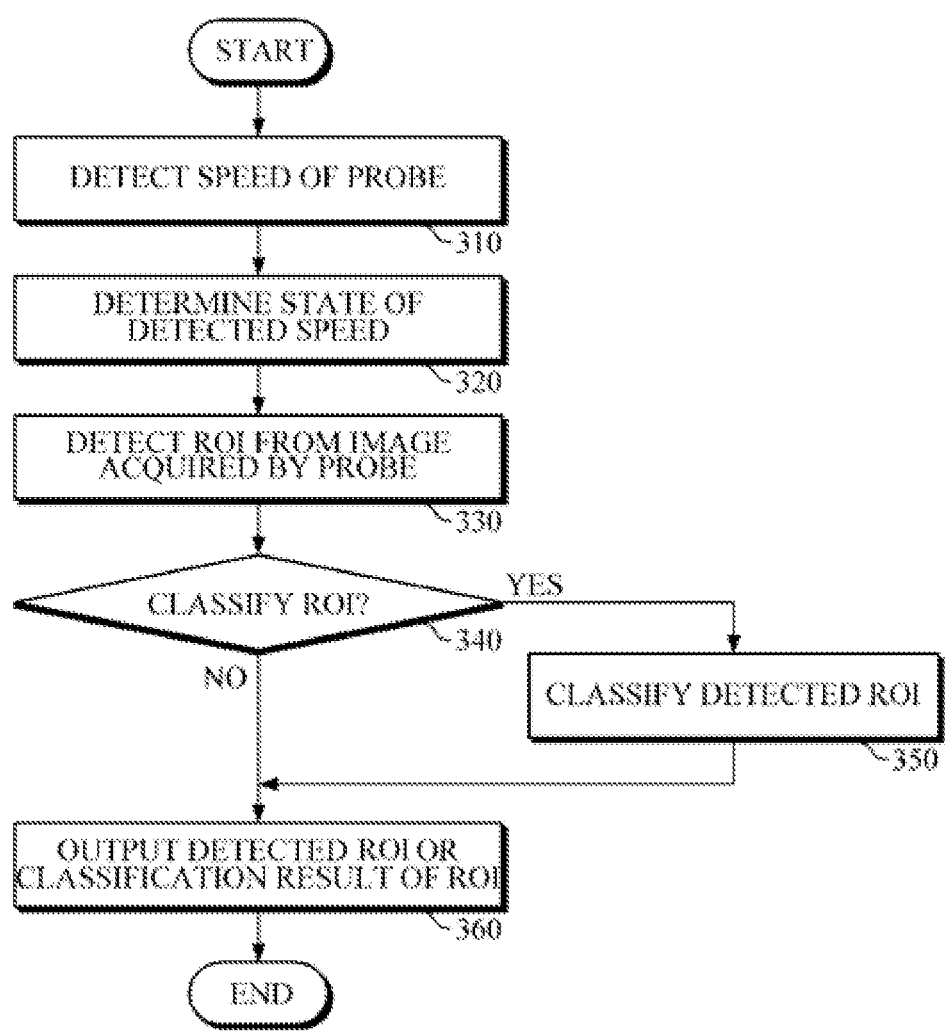
FIG. 5 is a flowchart illustrating a method for supporting CAD according to an example.
Figure 6:
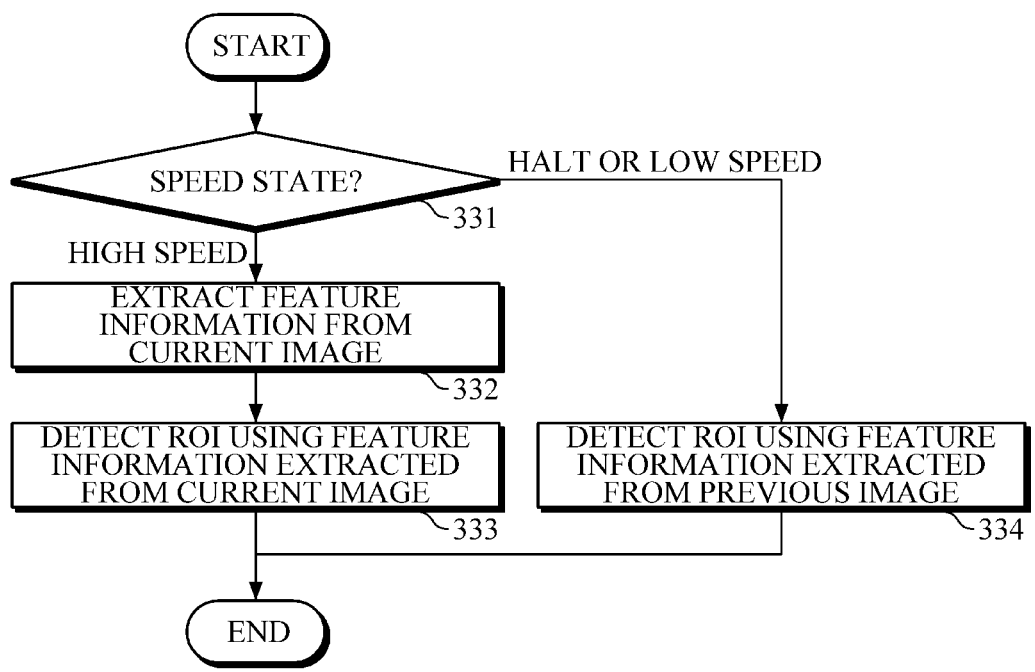
FIG. 6 is a flowchart illustrating an ROI detecting operation in the method shown in FIG. 5.

FIG. 5 is a flowchart illustrating a method for supporting CAD according to an example. FIG. 6 is a flowchart illustrating a process of detecting an ROI in the method shown in FIG. 5.

FIGS. 5 and 6 are examples of a method implemented by the apparatus 100 shown in FIG. 1.

Referring to FIG. 5, in operation 310, the method detects a speed of the probe. For example, when a user captures images of a patient's body by moving a probe, the apparatus 100 detects a speed of the probe in 310. At this point, the apparatus 100, in various examples, detects the speed of the probe using an accelerometer included in the probe, or the like. Alternatively, the apparatus 100 detects the speed of the probe based on a change in images acquired by the probe.

Such a change in images potentially includes information on difference in sums of image intensity for pixels between previous and current image, for example, a previous frame (t−1) and the current frame (t). In addition, in various examples, the change in images includes information on difference or similarity in histograms between previous and current images. In examples, a histogram is generated based on frequency of each pixel extracted from the entire area or a specific area of a frame image, and a speed of a probe is detected based on difference in frequencies or similarity in histograms. In addition, in examples, the change in images includes information on a change in primary information, such as information on a salient region, between previous and current images.

Then, in operation 320, the method determines a state of the detected speed. For example, when the speed of the probe is detected, the apparatus 100 determines a state of the detected speed. At this point, a state of speed is determined to be one of a halted state, a low speed state, and a high speed state according to a predetermined threshold, as described above.

Then, in operation 330, the method detects an ROI form an image acquired by the probe. For example, the apparatus 100 detects an ROI from an image received by the probe.

Hereinafter, detailed descriptions about operation 330 are provided with reference to the example of FIG. 6. Referring to the example of FIG. 6, in operation 331, the method checks a speed state of the probe. For example, the apparatus 100 checks a speed state of the probe. Then, the apparatus 100 only detects an ROI in a case of a high speed state, so that in operation 332 the method extracts feature information from a current image and the method detects the ROI using feature image. For example, the apparatus 100 extracts feature information from an image captured at the current time (t). The apparatus also detects the ROI based on the extracted feature information of the current time (t).

Alternatively, in operation 334, the method detects an ROI using feature information extracted from a previous image. For example, the apparatus 100 both detects and classifies an ROI in a case of a low speed state or a halted state, so that the apparatus 100 detects the ROI by utilizing location information of an ROI detected from images that are acquired at previous times (t−1, t−2, . . . ) or by utilizing feature information extracted from the previous images in 334. At this point in time, an ROI is detected from the current image using feature information by extracting the feature information from some part of the current image based on location information of a previous image instead of searching the entire area of the current image. As a result, the processing requirements to process the current image decrease.

Again, referring to the example of FIG. 5, in operation 340 the method determines whether to classify the ROI based on the determined speed state. For example, the apparatus 100 determines whether to classify the ROI based on the determined speed state. Thus, in a case where a speed state is determined as a halted state or a low speed state in 320, the apparatus 100 makes a determination to classify an ROI, and thus, classifies the ROI in operation 330. At this point in the method, a classification result optionally includes additional feature information, such as information on benignancy/malignancy, BI-RADS, and the like.

In a case where a speed state is determined as being a high speed in operation 320, in operation 360 the method outputs the detected ROI on the screen in 360, without classifying the ROI. For example, the apparatus 100 simply displays the detected ROI on the screen, without classifying the ROI. In addition, in a case where the detecting process in 330 and the classifying process in 350 are performed on the ROI because a speed state is determined as a halted state or a low speed state, in operation 360 the method outputs the detected ROI and a classification result thereof together on the screen. For example, the apparatus 100 outputs the detected ROI and a classification result thereof together on the screen. At this point, the apparatus 100 optionally also outputs, on the screen, information indicative of a current diagnostic process, for example, a detecting process or a classifying process, according to a speed state.

Figure 7:
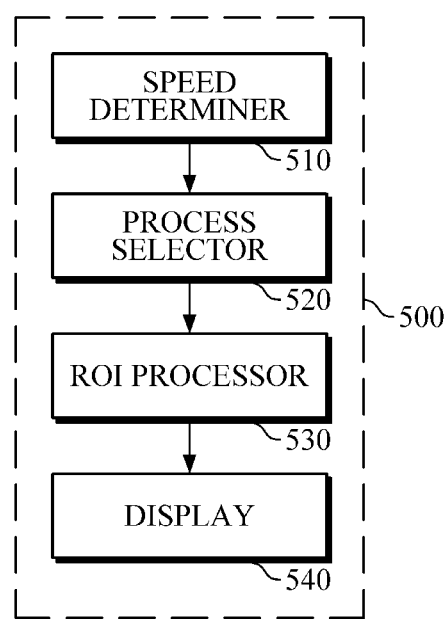
FIG. 7 is a block diagram illustrating an apparatus for supporting CAD according to another example.

FIG. 7 is a block diagram illustrating an apparatus for supporting CAD according to another example.

Referring to FIG. 7, an apparatus 500 for supporting CAD according to another example includes a speed determiner 510, a process selector 520, an ROI processor 530, and a display 540. However, this is only one example, and other examples include additional appropriate components in addition or instead of these components.

When a user moves a probe to examine a patient's body, the speed determiner 510 detects a speed of the probe and determines a state of the speed. As described above with reference to Table 1, in an example the speed state is determined as one of a halted state, a low speed state, or a high speed state. At this point in time, speed states of various stages are predetermined by setting various threshold intervals to help classify the state of the speed appropriately.

According to the determined speed state, the process selector 520 selects one of a process of only detecting an ROI, a process of only classifying an ROI, and a process of both detecting and classifying an ROI. At this point, detecting an ROI includes tracking the first detected ROI.

For example, in a case where a speed state is determined as a high speed state, the apparatus 100 selects a process of only detecting an ROI from an image acquired from a probe. In another example, in a case where a speed state is determined as a halted state or a low speed state, the apparatus 100 selects a process of only classifying an ROI or a process of both detecting and classifying an ROI according to a preset policy.

At this point, in an example, the preset policy is set based on various standards, for example, computing performance of a CAD system that analyzes an image received from a probe. That is, based on the capabilities and performance of a system, it is possible to set the apparatus 100 to both detect and classify an ROI, and in other cases, it is possible to set the apparatus 100 to only classify an ROI. For example, a high performance system with many resources is able to both detect and classify an ROI, but a system with lower performance and fewer resources is only able to classify the ROI. Alternatively, by setting a speed state at various stages, it is possible to set the apparatus 100 to select one of a process of detecting an ROI, a process of detecting and classifying an ROI, or a process of classifying an ROI.

The ROI processor 530 performs a process selected by the process selector 520. That is, in a case where a process of detecting an ROI is selected by the process selector 520, the ROI processor 530 extracts feature information from a received image and detects an ROI. In addition, in a case where a process of detecting and classifying an ROI or a process of detecting an ROI is selected by the process selector 520, the ROI processor 530 performs the selected process to generate a result of detecting or classifying an ROI.

When the ROI processor 540 performs a process selected by the process selector 520 and generates a corresponding result, that is, a detected ROI or a classification result of the ROI, display 540 outputs the generated result on a screen. At this point, if the process of only detecting an ROI is performed, the display 540 outputs, on the screen, a distinguished marker that indicates an ROI, and, if the process of both detecting and classifying an ROI is performed, the display 540 displays both an ROI and a classification result thereof on the screen. In addition, the display 540 outputs, on the screen, information indicative of the current process, and, if necessary, a detected speed or determined speed state information.

Figure 8:
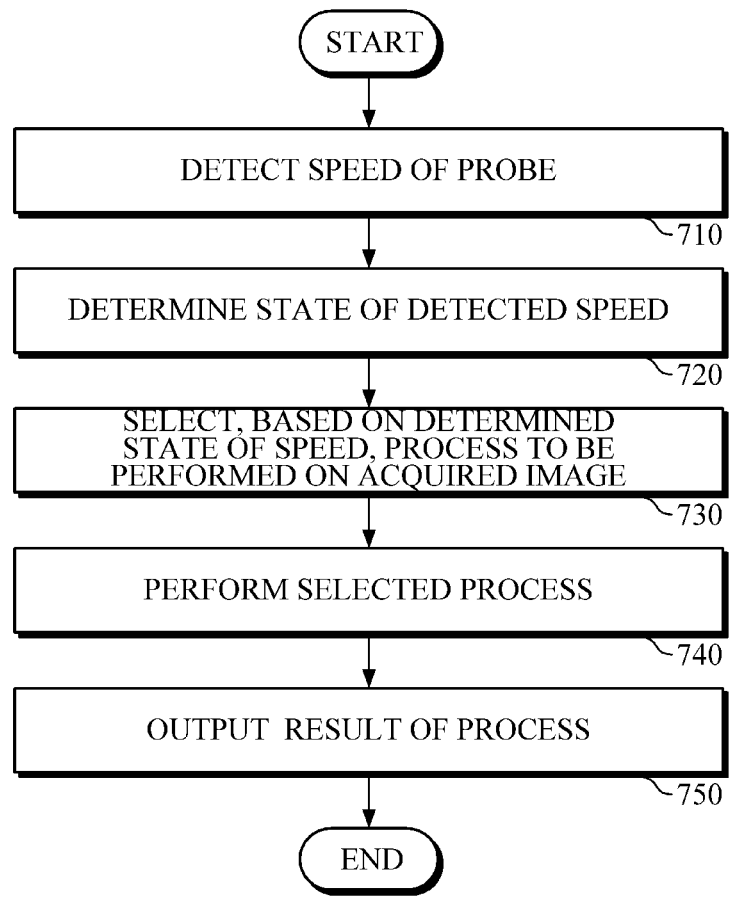
FIG. 8 is a flowchart illustrating a method for supporting CAD according to another example.
Figure 9:
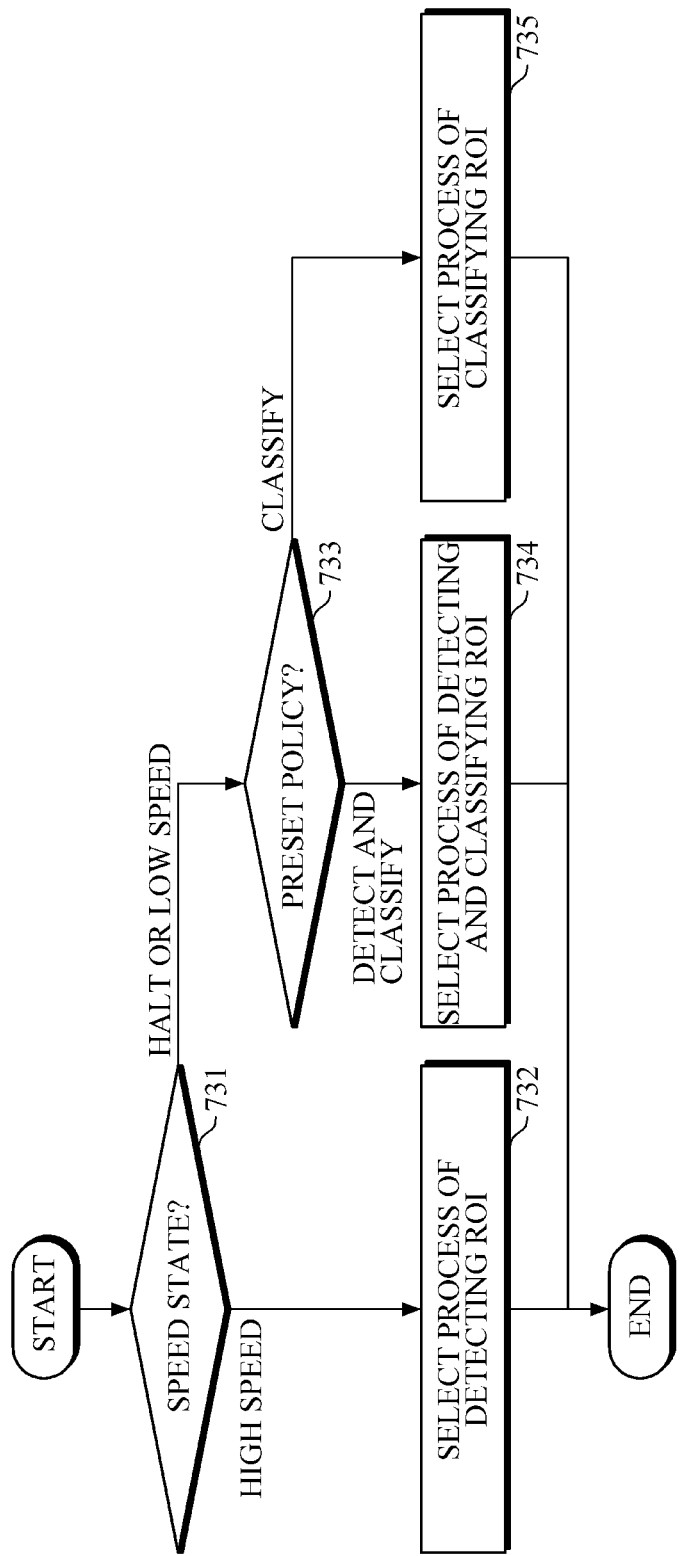
FIG. 9 is a flowchart illustrating an ROI detecting operation in the method shown in FIG. 8.

FIG. 8 is a flowchart illustrating a method for supporting CAD according to another example. FIG. 9 is a flowchart illustrating a process of detecting an ROI in the method shown in FIG. 8.

FIGS. 8 and 9 are examples of a method implemented by the apparatus 500 shown in FIG. 7.

Referring to FIG. 8, in operation 710, the method detects a speed of the probe. For example, the apparatus 500 detects speed of a probe. In operation 720, the method determines a state of the detected speed. For example, the apparatus determines a state of the detected speed. As described above, the speed of a probe is detected, for example, by using a change in images received from a probe or by using an accelerometer equipped in the probe, or another appropriate sensor. In addition, the speed state is determined as one of halt, low, or high, by comparing the detected speed with a predetermined threshold.

Then, in operation 730, the method, according to the determined speed state, the method the apparatus 500 selects a process to be performed on the received image. For example, the apparatus 500 selects a process to be performed on the received image. In examples, the process to be performed includes a process of only detecting an ROI, a process of both detecting and classifying an ROI, and a process of only classifying an ROI.

Further, additional detailed descriptions about operation 730 are provided with reference to FIG. 9. Referring to FIG. 9, in operation 731, the method checks a speed state. For example, the apparatus 500 checks a speed state. If the speed state indicates high speed, in operation 732, the method selects a process of only detecting an ROI. For example, the apparatus 500 selects a process of only detecting an ROI.

Alternatively, in operation 733, if the speed state indicates halt or low speed, the method checks whether there is a preset policy. For example, the apparatus 500 checks whether there is a preset policy. In operation 734, if the preset policy is detection and classification, the method selects a process of both detecting and classifying an ROI. For example, if the preset policy is detection and classification, the apparatus 500 selects a process of both detecting and classifying an ROI. In operation 735, if the preset policy is classification, the method selects a process of only classifying an ROI. For example, the apparatus 500 selects a process of only classifying an ROI.

Again, referring to the example of FIG. 8, when any one process is selected in operation 730, in operation 740 the method performs the selected process. For example, the apparatus 500 generates a corresponding result by performing the selected process. That is, in the process of detecting an ROI, or the process of detecting and classifying an ROI, the apparatus 500 extracts various kinds of feature information and detect an ROI using the feature information. In addition, in the process of classifying an ROI, or the process of detecting and classifying an ROI, the apparatus 500 generates a classification result as to whether a lesion is benign or malignant by classifying a detected ROI.

In a case where the process of detecting and classifying an ROI is selected by the method in operation 730 where the speed state is determined as halt or high, the method classifies an ROI by utilizing feature information extracted from a previous information for a purpose of detection of an ROI and by extracting additional feature information from the current image, which is necessary to classify the ROI. For example, the apparatus 500 classifies an ROI by utilizing feature information extracted from previous information for a purpose of detection of an ROI and by extracting additional feature information from the current image, which is necessary to classify the ROI.

Then, in operation 750, the method outputs the generated result on a screen. For example, the apparatus 500 outputs the generated result on a screen. Thus, in a case where the process of only detecting an ROI is performed in operation 740, the apparatus 500 may output a distinguished marker indicative of an ROI on an image output on the screen. In a case where the process of detecting and classifying an ROI or the process of classifying an ROI, the apparatus 500 displays any previously or currently detected ROI while outputting a classification result thereof at a specific location on the screen.

The image display apparatus described herein may be implemented using a liquid crystal display (LCD), a lightemitting diode (LED) display, a plasma display panel (PDP), a screen, a terminal, or any other type of display known to one of ordinary skill in the art. A screen may be a physical structure that includes one or more hardware components that provide the ability to render a user interface and receive user input. The screen may include any combination of a display region, a gesture capture region, a touch-sensitive display, and a configurable area. The screen may be part of an apparatus, or may be an external peripheral device that is attachable to and detachable from the apparatus. The display may be a single-screen display or a multi-screen display. A single physical screen may include multiple displays that are managed as separate logical displays permitting different content to be displayed on separate displays even though they are part of the same physical screen.

The user interface may provide the capability of inputting and outputting information regarding a user and an image. The user interface may include a network module for connecting to a network and a universal serial bus (USB) host module for forming a data transfer channel with a mobile storage medium. In addition, the user interface may include one or more input/output devices, such as a mouse, a keyboard, a touch screen, a monitor, a speaker, a screen, or a software module for controlling the input/output device.

The apparatuses, units, modules, devices, and other components illustrated in FIGS. 1-9 that perform the operations described herein with respect to FIGS. 1-9 are implemented by hardware components. Examples of hardware components include controllers, sensors, generators, drivers, and any other electronic components known to one of ordinary skill in the art. In one example, the hardware components are implemented by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 1-9. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-9 that perform the operations described herein with respect to FIGS. 1-9 are performed by a processor or a computer as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

As a non-exhaustive example only, a terminal/device/unit as described herein may be a mobile device, such as a cellular phone, a smart phone, a wearable smart device (such as a ring, a watch, a pair of glasses, a bracelet, an ankle bracelet, a belt, a necklace, an earring, a headband, a helmet, or a device embedded in clothing), a portable personal computer (PC) (such as a laptop, a notebook, a subnotebook, a netbook, or an ultra-mobile PC (UMPC), a tablet PC (tablet), a phablet, a personal digital assistant (PDA), a digital camera, a portable game console, an MP3 player, a portable/personal multimedia player (PMP), a handheld e-book, a global positioning system (GPS) navigation device, or a sensor, or a stationary device, such as a desktop PC, a high-definition television (HDTV), a DVD player, a Blu-ray player, a set-top box, or a home appliance, or any other mobile or stationary device capable of wireless or network communication. In one example, a wearable device is a device that is designed to be mountable directly on the body of the user, such as a pair of glasses or a bracelet. In another example, a wearable device is any device that is mounted on the body of the user using an attaching device, such as a smart phone or a tablet attached to the arm of a user using an armband, or hung around the neck of the user using a lanyard.

A computing system or a computer may include a microprocessor that is electrically connected to a bus, a user interface, and a memory controller, and may further include a flash memory device. The flash memory device may store N-bit data via the memory controller. The N-bit data may be data that has been processed and/or is to be processed by the microprocessor, and N may be an integer equal to or greater than 1. If the computing system or computer is a mobile device, a battery may be provided to supply power to operate the computing system or computer. It will be apparent to one of ordinary skill in the art that the computing system or computer may further include an application chipset, a camera image processor, a mobile Dynamic Random Access Memory (DRAM), or any other device known to one of ordinary skill in the art as being suitable for inclusion in a computing system or computer. The memory controller and the flash memory device may constitute a solid-state drive or disk (SSD) that uses non-volatile memory to store data.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An apparatus to support computer aided diagnosis (CAD), comprising:
    a probe configured to transmit and receive an ultrasound signal;
    a display;
    a memory configured to store instructions therein; and
    at least one processor, upon execution of the instructions stored on the memory, configured to:
        generate at least one image using the probe,
        control the display to display a current image of the at least one image on a screen,
        detect a speed of the probe and determine a state of the speed of the probe,
        detect a region of interest (ROI) from the current image,
        in response to detecting the ROI from the current image, control the display to display a distinguished marker indicative of the detected ROI at a corresponding location in the current image using location information of the detected ROI,
        determine whether to classify the detected ROI based on the determined state of the speed of the probe, and
        classify the detected ROI at the time of detection in response to a result of the determination is determined to classify the detected ROI,
    wherein the speed of the probe is determined based on a change between the generated images.

2. The apparatus of claim 1, wherein the change between the generated images comprises at least one of:
    a difference in sums of image intensity for each pixel between the current image and a previous image,
    a difference in histograms between the current image and the previous image,
    a similarity in histograms between the current image and the previous image, or
    a degree of change in primary information between the currently acquired image and the previously acquired image.

3. The apparatus of claim 1, wherein the at least one processor is further configured to:
    compare the detected speed to a preset threshold, and
    determine the state of the detected speed as being one of a halted state, a low speed state, or a high speed state.

4. The apparatus of claim 3, wherein the at least one processor is further configured to:
    extract feature information from the current image in a case where the determined state of the speed is the high speed state,
    extract feature information from the area to be searched in the current image which is determined based on at least one of information on an area searched in the previous image or information on an ROI extracted from the previous image in a case where the determined state of the speed is the halted state or the low speed state, and
    detect the ROI using the feature information.

5. The apparatus of claim 3, wherein, in a case where the state of the detected speed is the halted state or the low speed state, the at least one processor is further configured to:
    determine to classify the ROI,
    extract feature information from the current image, and
    classify the ROI using the extracted feature information.

6. The apparatus of claim 1, wherein, in a case where the determined state of the speed is a halted state or a low speed state, the display is further configured to:
    output the distinguished marker at the corresponding location in the current image on the screen using location information of an ROI detected from an image previous to the current image.

7. The apparatus of claim 1, wherein, in response to classification being performed on the ROI, the display is further configured to:
    output a classification result on a specific location on the screen or output the classification result so as to overlap the current image on the screen.

8. The apparatus of claim 1, wherein the display is further configured to output an information item indicative of the detected speed, the determined state of the speed, or a current diagnostic process.

9. A method to support computer aided diagnosis (CAD), comprising:
    generating, by at least one processor, at least one image using a probe;
    controlling, by at least one processor, a display to display a current image of the at least one image on a screen;
    detecting, by the at least one processor, a speed of the probe;
    determining, by the at least one processor, a state of the speed of the probe;

detecting, by the at least one processor, a region of interest (ROI) from the current image;

in response to detecting the ROI from the current image, controlling, by at least one processor, the display to display a distinguished marker indicative of the detected ROI at a corresponding location in the current image using location information of the detected ROI;

determining, by the at least one processor, whether to classify the detected ROI based on the state of the speed of the probe; and classifying, by the at least one processor, the detected ROI at the time of detection in response to a result of the determination is determined to classify the detected ROI, wherein the detecting of the speed of the probe comprises determining the speed of the probe based on a change between the generate images.

10. The method of claim 9, wherein the determining of the state of the speed of the probe comprises:

comparing the speed to a preset threshold, and determining the state of the speed as being one of a halted state, a low speed state, or a high speed state.

11. The method of claim 10, wherein the detecting of the ROI comprises:

extracting feature information from the current image in a case where the state of the speed is determined to be the high speed state;

extracting feature information from the determined area to be searched in the current image which is determined based on at least one of information on an area searched in the previous image or information on an ROI detected from the previous image in a case where the state of the speed is determined to be the halted state or the low speed state; and detecting the ROI using the extracted feature information.

12. The method of claim 10, wherein the determining of whether to classify the detected ROI comprises:

determining to classify the detected ROI in response to the state of the speed being determined as the halted state or the low speed state and in response to a determination to classify the detected ROI;

extracting feature information; and classifying the detected ROI using the extracted feature information.

13. The method of claim 9, wherein, in a case where the state of the speed is a halted state or a low speed, the outputting of a distinguished marker comprises:

outputting the distinguished marker indicative of the ROI at the corresponding location in the current image on the screen using location information of an ROI detected from the previous image.

14. The method of claim 9, wherein, in response to classification being implemented on the ROI, the classifying of the ROI comprises:

outputting a classification result of the ROI at a specific location on a screen or outputting the classification result of the ROI so as to overlap the current image on the screen.

* * * * *